(12) United States Patent
Callahan et al.

(10) Patent No.: US 12,702,811 B2
(45) Date of Patent: Aug. 11, 2026

(54) FLUID CONNECTOR ASSEMBLY

(71) Applicant: CareFusion 303, Inc., San Diego, CA (US)

(72) Inventors: Ryan Callahan, Long Beach, CA (US); Frank Cai, Ontario, CA (US)

(73) Assignee: CAREFUSION 303, INC., San Diego, CA (US)

( * ) Notice: Subject to any disclaimer, the term of this patent is extended or adjusted under 35 U.S.C. 154(b) by 269 days.

(21) Appl. No.: 18/350,840

(22) Filed: Jul. 12, 2023

(65) Prior Publication Data

US 2025/0018165 A1 Jan. 16, 2025

(51) Int. Cl.
*A61M 39/14* (2006.01)
*A61M 39/26* (2006.01)
*A61M 39/10* (2006.01)

(52) U.S. Cl.
CPC ............ *A61M 39/14* (2013.01); *A61M 39/26* (2013.01); *A61M 2039/1027* (2013.01); *A61M 2039/1066* (2013.01); *A61M 2039/1072* (2013.01); *A61M 2039/267* (2013.01)

(58) Field of Classification Search
CPC .......... A61M 39/14; A61M 2039/1027; A61M 39/1011; A61M 39/10; A61M 2039/1066; A61M 2039/1072; A61M 39/26; A61M 2039/267; A61M 5/162; A61M 39/22; A61M 2039/1016; A61M 2039/1033
See application file for complete search history.

(56) References Cited

U.S. PATENT DOCUMENTS

| | | | | |
|---|---|---|---|---|
| 5,713,856 A | 2/1998 | Eggers et al. | | |
| 6,170,522 B1 * | 1/2001 | Tanida | F16L 39/00 | 137/614.04 |
| 6,874,522 B2 | 4/2005 | Anderson et al. | | |

(Continued)

FOREIGN PATENT DOCUMENTS

| | | |
|---|---|---|
| EP | 1678070 A2 | 7/2006 |
| EP | 1517723 B1 | 1/2007 |

(Continued)

OTHER PUBLICATIONS

International Search Report and Written Opinion for Application No. PCT/US2024/037206, dated Oct. 1, 2024, 11 pages.

(Continued)

*Primary Examiner* — Susan S Su
(74) *Attorney, Agent, or Firm* — MASCHOFF BRENNAN

(57) ABSTRACT

Fluid connector assemblies that seal off fluid paths in the respective connectors are disclosed. When connectors of a fluid connector assembly are connected to each other, respective compressible members in the connectors are displaced, allowing downstream fluid passage through the fluid connector assembly. The connectors maintain a connection by a snap mechanism that provides a threshold retention force. When an external force greater than the threshold force is applied to the fluid connector assembly, the snap mechanism may no longer maintain the connectors together, causing the connectors to decouple from each other. Once the connectors are decoupled, a connecting mechanism may be activated preventing the connectors to be coupled together without actuation of the connecting mechanism.

19 Claims, 7 Drawing Sheets

(56) References Cited

U.S. PATENT DOCUMENTS 7,004,934 B2 2/2006 Vaillancourt
7,040,598 B2 5/2006 Raybuck
7,153,296 B2 12/2006 Mitchell
7,350,764 B2 4/2008 Raybuck
7,396,051 B2 7/2008 Baldwin et al.
7,763,013 B2 7/2010 Baldwin et al.
7,766,394 B2 8/2010 Sage et al.
7,794,675 B2 9/2010 Lynn
7,803,139 B2 9/2010 Fangrow, Jr.
7,803,140 B2 9/2010 Fangrow, Jr.
7,815,614 B2 10/2010 Fangrow, Jr.
7,918,243 B2 4/2011 Diodati et al.
7,998,134 B2 8/2011 Fangrow et al.
8,123,738 B2 2/2012 Vaillancourt
8,142,418 B2 3/2012 Mcmichael et al.
8,211,069 B2 7/2012 Fangrow, Jr.
8,262,628 B2 9/2012 Fangrow, Jr.
8,361,408 B2 1/2013 Lynn
8,480,968 B2 7/2013 Lynn
8,777,908 B2 7/2014 Fangrow, Jr.
8,777,909 B2 7/2014 Fangrow, Jr.
8,795,256 B1 8/2014 Smith
8,888,758 B2 11/2014 Mansour
8,899,267 B2 12/2014 Diodati et al.
8,910,919 B2 12/2014 Bonnal et al.
8,974,425 B2 3/2015 Tachizaki et al.
8,974,437 B2 3/2015 Williams et al.
9,114,242 B2 8/2015 Fangrow et al.
9,126,028 B2 9/2015 Fangrow et al.
9,126,029 B2 9/2015 Fangrow et al.
9,192,753 B2 11/2015 Lopez et al.
9,234,616 B2 1/2016 Carrez et al.
9,358,379 B2 6/2016 Fangrow, Jr.
9,433,769 B2 9/2016 Bayly
9,468,749 B2 10/2016 Mansour et al.
9,492,649 B2 11/2016 Carrez et al.
9,636,492 B2 5/2017 Fangrow, Jr.
9,724,504 B2 8/2017 Fangrow, Jr. et al.
9,724,505 B2 8/2017 Williams et al.
9,861,805 B2 1/2018 Dennis et al.
9,933,094 B2 4/2018 Fangrow
9,974,939 B2 5/2018 Fangrow, Jr.
9,974,940 B2 5/2018 Fangrow, Jr.
10,029,086 B2 7/2018 Nowak et al.
10,156,306 B2 12/2018 Fangrow
10,173,045 B2 1/2019 Mansour
10,179,203 B1 1/2019 Huslage et al.
10,315,025 B2 6/2019 Phillips et al.
10,398,887 B2 9/2019 Fangrow, Jr. et al.
10,441,507 B2 10/2019 Sanders
10,518,078 B2 12/2019 Stjernberg Bejhed et al.
10,569,073 B2 2/2020 Hallisey et al.
10,625,068 B2 4/2020 Leuthardt et al.
10,655,768 B2 5/2020 Jones et al.
10,697,570 B2 6/2020 Fangrow
10,744,315 B2 8/2020 Sanders
10,842,982 B2 11/2020 Fangrow, Jr.
10,857,346 B2 12/2020 Dennis et al.
10,864,362 B2 12/2020 Jones et al.
10,881,847 B2 1/2021 Lynn
11,168,818 B2 11/2021 Fangrow
11,207,514 B2 12/2021 Kakinoki
11,235,135 B2 2/2022 Tsai
11,273,297 B2 3/2022 Kakinoki
11,484,471 B2 11/2022 Sanders
11,491,084 B2 11/2022 Ueda et al.
2004/0215158 A1 10/2004 Anderson
2005/0090805 A1 4/2005 Shaw et al.
2006/0129109 A1 6/2006 Shaw et al.
2007/0088292 A1 4/2007 Fangrow, Jr.
2007/0088293 A1 4/2007 Fangrow, Jr.
2007/0088294 A1 4/2007 Fangrow, Jr.
2007/0225635 A1 9/2007 Lynn
2008/0039803 A1 2/2008 Lynn
2008/0065000 A1 3/2008 Bidinger et al.
2008/0287920 A1* 11/2008 Fangrow .............. A61M 39/26 604/535
2011/0106046 A1 5/2011 Hiranuma
2014/0249487 A1 9/2014 Lynn
2014/0330254 A1 11/2014 Rosenberger et al.
2016/0000363 A1 1/2016 Jones et al.
2018/0200147 A1 7/2018 Sanders
2019/0184152 A1 6/2019 Kakinoki
2019/0282797 A1 9/2019 Tsai
2020/0113784 A1 4/2020 Lopez et al.
2020/0179672 A1 6/2020 Kakinoki
2020/0215319 A1 7/2020 Fangrow, Jr. et al.
2020/0284385 A1 9/2020 Fangrow
2020/0323734 A1 10/2020 Ueda et al.
2020/0338331 A1 10/2020 Sanders
2021/0069484 A1 3/2021 Tsai
2021/0077803 A1 3/2021 Lynn
2021/0252267 A1 8/2021 Fangrow, Jr.
2021/0388926 A1 12/2021 Martin et al.
2021/0393938 A1 12/2021 Lynn et al.
2022/0260189 A1 8/2022 Deuse
2022/0282814 A1 9/2022 Fangrow
2023/0048460 A1 2/2023 Tachizaki

FOREIGN PATENT DOCUMENTS

EP 1622675 B1 8/2009
EP 2144634 A1 1/2010
EP 2298407 A1 3/2011
EP 2694132 A1 2/2014
EP 2562456 B1 6/2014
EP 2782633 A1 10/2014
EP 1842002 B1 4/2015
EP 2736582 B1 5/2015
EP 2089094 B1 1/2016
EP 2219721 B1 12/2017
EP 2753396 B1 12/2017
EP 2736584 B1 4/2018
EP 3305361 A1 4/2018
EP 2271398 B1 11/2018
EP 2480281 B1 11/2018
EP 2790750 B1 11/2018
EP 2331191 B1 3/2019
EP 3079756 B1 3/2019
EP 2121114 B1 5/2019
EP 2719419 B1 5/2019
EP 2956204 B1 8/2019
EP 3421077 B1 8/2019
EP 3530313 A1 8/2019
EP 3538201 A1 9/2019
EP 3570807 A1 11/2019
EP 3570809 A1 11/2019
EP 2536463 B1 4/2020
EP 3381505 B1 5/2020
EP 3538201 B1 5/2020
EP 1904152 B1 12/2020
EP 2150307 B1 12/2020
EP 3313490 B1 1/2021
EP 3760275 A1 1/2021
EP 3851155 A1 7/2021
EP 3517164 B1 9/2021
EP 3954355 A1 2/2022
EP 3960229 A1 3/2022
EP 3973044 A1 3/2022
EP 3305361 B1 5/2022
EP 3134052 B1 8/2022
EP 3530313 B1 8/2022
WO WO-2021099437 A1 5/2021
WO WO-2021180675 A1 9/2021
WO WO-2021252197 A1 12/2021
WO WO-2022042956 A1 3/2022
WO WO-2022149339 A1 7/2022
WO WO-2022207560 A1 10/2022

OTHER PUBLICATIONS

Bangert, Bill, "Shorter times to blood transfusion associated with decreased death risk in trauma patients", Medical Xpress, Apr. 14,

(56) References Cited

OTHER PUBLICATIONS 2016, https://medicalxpress.com/news/2016-04-shorter-blood-transfusion-decreased-death.html.
Icumedical, "ChemoClave™ Needlefree Close System Transfer Device (CSTD)", date unknown, https://www.icumed.com/products/oncology/closed-system-transfer-devices/chemoclave.
Icumedical, "ChemoLock™ Needlefree Closed System Transfer Device (CSTD)", date unknown, https://www.icumed.com/products/oncology/closed-system-transfer-devices/chemolock.
Ivteam, "Force-activated separation IV connectors", 2022, Retrieved from the internet https://www.ivteam.com/intravenous-literature/force-activated-separation-iv-connectors/ [Last retrieved Jan. 13, 2023].
Lineus Medical, SafeBreak Product Features and Benefits Brochure, May 2021, mkg 0058 May 2021 Rev. 02.
Przen, "Lineus Medical Goes International, Signs ONEY for Distribution in Korea", PRZen Online Press Release Distribution, PrZen/33448014, MKG-0130 Rev 00, Retrieved from the internet https://przen.com/pr/lineus-medical-goes-international-signs-oney-for-distribution-in-korea-przen-33448014 [Last retrieved Jan. 13, 2023].
Rickard, et al., "Securing All intraVenous devices Effectively in hospitalised patients—the SAVE trial: study protocol for a multicentre randomised controlled trial", BMJ Open, Sep. 23, 2015;5(9):e008689, doi: 10.1136/bmjopen-2015-008689. PMID: 26399574; PMCID: PMC4593168.
Tada Group AB, LinkedIn Post "ReLink granted patent in Japan", LinkedIn, Mar. 2022, retrieved from the internet https://se.linkedin.com/company/tadamedical?trk=public_post_reshare_feed-actor-image&original_referer= [Last retrieved Mar. 2022].
Tribology, "Coefficient of friction, Rolling resistance and Aerodynamics", date unknown, https://www.tribology-abc.com/abc/cof.htm.

* cited by examiner

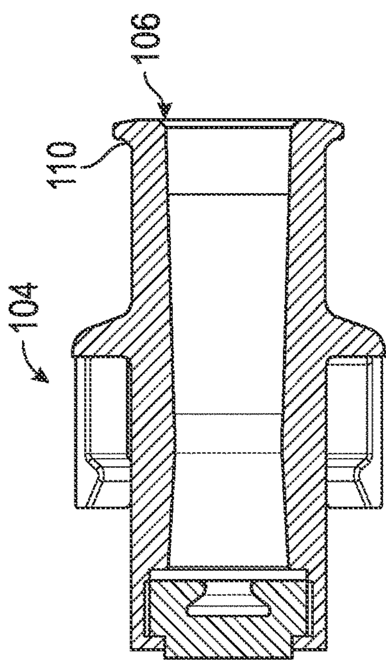
FIG. 2
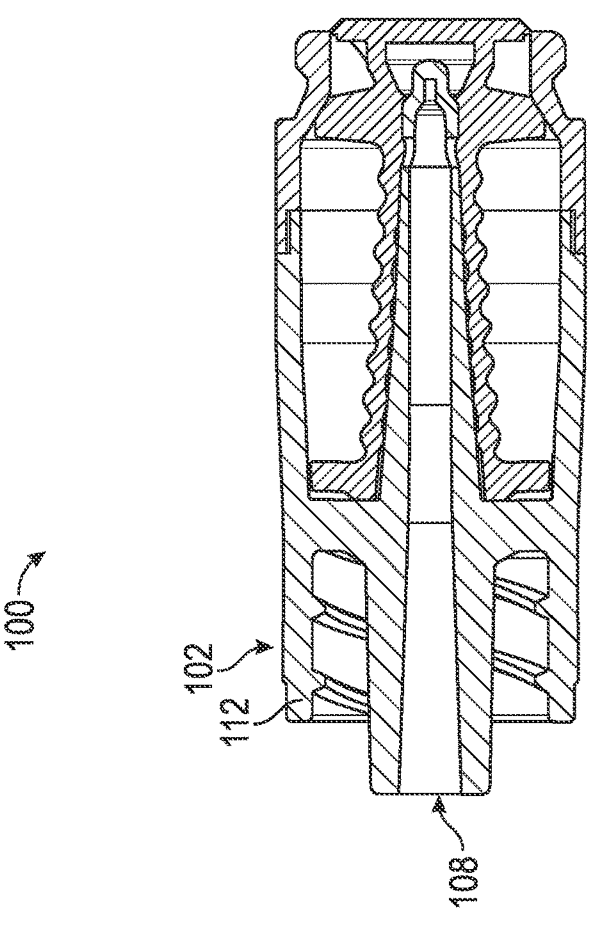

154
138
146B
150
128B
148
134B
144
134
140
132
120
142
134A
114B
136
126
146
146A
122
114
116
118
114A
102
124
128A
130
128
152

FLUID CONNECTOR ASSEMBLY

TECHNICAL FIELD

The present disclosure relates generally to medical fluid connectors and, more particularly, to a fluid connector assembly that includes medical connectors that decouple with each other due to an applied force, with each medical connector designed to automatically seal off their respective fluid paths. The decoupling may be due to intentional or unintentional separation between the medical connectors.

BACKGROUND

Peripheral intravenous ("PIVC") catheters are medical tools inserted into peripheral veins of patients to deliver medical fluid to the patients. In an example application, the medical fluid is delivered to the patient, and a medical professional subsequently removes the PIVC catheter from the patient. Often, however, these catheters are unintentionally dislodged. For example, catheter lines receiving an unintended or unexpected pulling force can pull the IV tubing, which pulls the catheter out of the patient. In other instances, catheters are accidentally removed from patients and medical professionals. Unintended or unexpected dislodgement can lead to patient blood loss, IV fluid loss, and IV fluid delivery delay.

SUMMARY

In accordance with at least some embodiments disclosed herein is the realization that unintended dislodgement or disconnection of a medical connection, such as a medical fluid line, can result in injury to a patient or a medical professional, such as by depriving the patient of a medicament, increasing the potential for infection to the patient, and exposing the medical professional to medicaments.

Aspects of the present disclosure provide fluid connector assemblies with medical connectors, each of which include one or more fluid paths, that respond to unintentional or unexpected external forces by decoupling from each other and sealing off their respective fluid paths. The decoupling may include automatic decoupling using bellows or other elastically compressible member that decompress and return to their original shape external forces are no longer acting upon them. Beneficially, fluid connector assemblies described herein can limit or prevent patient blood loss, IV fluid loss, infection, and medical delivery delays. Further, aspects of the present disclosure provide connecting mechanisms that aid in the connection of the fluid connector assembly in the event that the fluid connector assembly is decoupled.

According to certain embodiments, a fluid connector assembly includes a first connector, a second connector, and a connecting mechanism. The first connector may include a first housing having a cavity, a post disposed in the first housing and having an opening, and a first compressible member surrounding at least a portion of the post. The second connector may be configured to couple with the first connector and include a second housing and a second compressible member disposed within the second housing. The connecting mechanism may be coupled to the second connector for coupling the first connector to the second connector and may include at least one projection extending from the second housing for actuating the connecting mechanism, wherein actuation of the at least one projection allows the first connector and the second connector to be coupled.

In some embodiments, the second connector is held in the cavity by a threshold force, and responsive to an external force, greater than the threshold force, applied to at least one of the first connector and the second connector that removes the second housing from the cavity: the first compressible member seals the first opening, and the second compressible member seals the second opening.

In some embodiments, the connecting mechanism further includes a biasing member for biasing the projection.

In some embodiments, the connecting member includes a stowed position and a deployed position. The connecting mechanism may be biased to the stowed position via the biasing member.

In some embodiments, the connecting mechanism further comprises at least one slot disposed on the second connector and proximate the at least one projection. When the first connector and the second connector are decoupled, the at least one projection may be urged to the deployed position via the biasing member such that the at least one projection moves into at least one slot.

In some embodiments, reconnection of the first connector and the second connector requires movement of the at least one projection out of the at least one slot.

In some embodiments, the projection includes a first end positioned within a gap formed between the at least one snap arm and the second housing and a second end opposite the first end. The projection may be positioned at an angle relative a longitudinal axis of the second connector and the first end may be positioned closer to the second housing than the second end. In the deployed position, the first end of the projection may be moved away from the second housing and the second end of the projection may be moved toward the second housing.

In some embodiments, the connecting mechanism further includes a handle for actuating the at least one projection and a cover portion for covering an engaging portion of the second connector. The handle may be disposed on a first end of the projection and the cover portion may be disposed on a second end of the projection opposite the handle. When a force is applied to the handle, the connecting mechanism may be actuated such that the at least one projection moves from a stowed position to a deployed position. In the deployed position, the cover portion may be actuated such that an end of the second compressible member is exposed thereby allowing the first connector and the second connector to be coupled.

According to certain embodiments, a method for coupling a fluid connector assembly includes providing a first connector, a second connector configured to couple to the first connector, and a connecting mechanism configured to couple to the first and second connectors. The first connector may include a first housing having a cavity, a post disposed in the first housing and having an opening, and a first compressible member for surrounding at least a portion of the post. The second connector may include a second housing and a second compressible member disposed within the second housing. The method may further include actuating the connecting mechanism, coupling the first connector and the second connector and releasing the connecting mechanism thereby allowing the connecting mechanism to retain the first connector and the second connector in the coupled state.

In some embodiments, the connecting mechanism includes at least one projection and at least one slot for receiving the at least one projection and actuating the connecting mechanism includes rotating the second connector such that the at least one projection is displaced from the at least one slot.

In some embodiments, the second connector includes at least one snap arm disposed on the second housing and the connecting mechanism includes at least one projection extending from the second housing proximate the at least one snap arm. Actuating the connecting mechanism may include applying a force to a first end of the at least one projection thereby causing the at least one projection to pivot and displace the at least one snap arm a distance away from the second housing. The connecting mechanism may further include a handle on a first end of the projection and a cover portion disposed on a second end opposite the first end. Moreover, actuating the connecting mechanism may further include applying a force to the handle thereby causing the cover portion to move relative an end of the second housing.

According to certain embodiments, a fluid connector assembly includes a first connector, a second connector configured to couple with the first connector, and a connecting mechanism coupled to the second connector for coupling the first connector and the second connector. The first connector may include a first housing having a cavity, a post disposed in the first housing and having an opening. The second connector may include a second housing, a second disposed within the second housing configured to contact the first compressible member when the first connector and second connector are coupled, and at least one snap arm disposed on an exterior surface of the second housing for retaining the fluid connector assembly in a coupled state. The connecting mechanism may include at least one projection extending from the at least one snap arm for actuating the connecting mechanism, the at least one projection having a stowed position and a deployed position. The projection may be moved toward the deployed position in response to an external force thereby actuating the connecting mechanism. When the first connector and the second connector are decoupled, actuation of the projection may be required to recouple the first and second connectors.

BRIEF DESCRIPTION OF THE DRAWINGS

Various features of illustrative embodiments of the inventions are described below with reference to the drawings. The illustrated embodiments are intended to illustrate, but not to limit, the inventions. The drawings contain the following figures:

FIG. 2 illustrates a partial cross-sectional view of the connector of the fluid connector assembly, in accordance with aspects of the present disclosure.

DETAILED DESCRIPTION

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present description sets forth specific details of various embodiments, it will be appreciated that the description is illustrative only and should not be construed in any way as limiting. Additionally, it is contemplated that although particular embodiments of the present disclosure may be disclosed or shown in the context of an IV set, such embodiments can be used in other fluid conveyance systems. Furthermore, various applications of such embodiments and modifications thereto, which may occur to those who are skilled in the art, are also encompassed by the general concepts described herein.

In accordance with some embodiments, the present disclosure includes various features and advantages of a fluid connector assembly with medical connectors that seal off their respective fluid paths when the medical connectors are decoupled from each other. The medical connectors may each include a compressible member that decompresses in response to the decoupling, thus providing an automatic sealing of the respective fluid paths. The fluid connector assembly may further include connecting mechanisms, which may function to prevent a patient from reconnecting the fluid connector assembly such that the respective surfaces may be properly disinfected.

Figure 1:
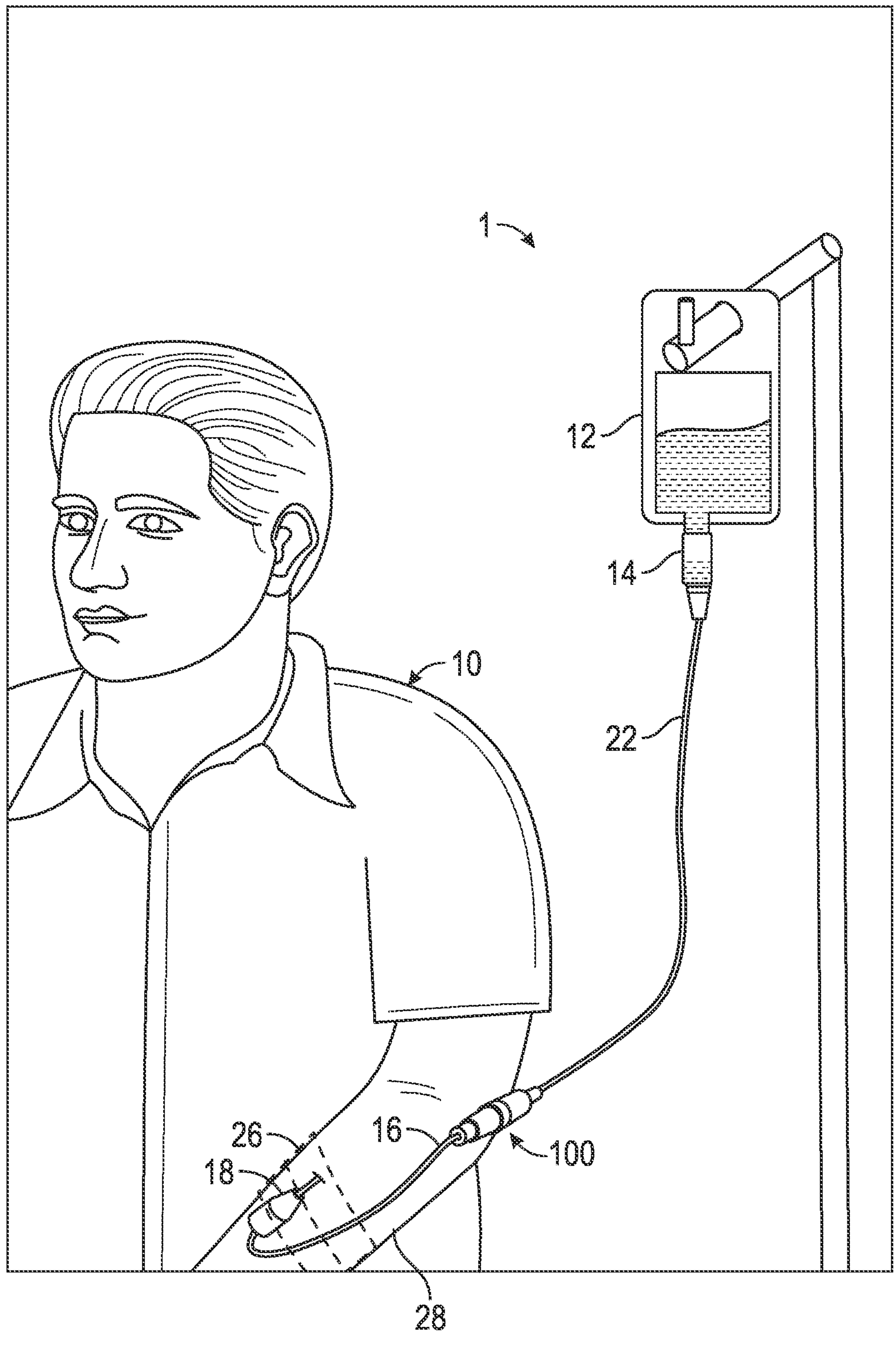
FIG. 1 illustrates an IV set coupled to a patient, in accordance with aspects of the present disclosure.

Referring now to the figures, FIG. 1 illustrates an IV set 1 coupled to a patient 10, in accordance with aspects of the present disclosure. The IV set 1 includes a medicament bag 12, a drip chamber 14, and tubing 22. The tubing 22 extends between the drip chamber 14 and a fluid connector assembly 100 of the IV set 1. To resist unintended dislodgement or disconnection of the tubing 16 or the catheter 18 from the patient, tape 26 is placed over the tubing 16 and the catheter 18, so that the tape 26 engages the tubing 16, the catheter 18, and the patient 10.

FIG. 2 illustrates a perspective view of a fluid connector assembly 100, in accordance with aspects of the present disclosure. The fluid connector assembly 100 is designed for use in medical applications, such as the IV set 1 (shown in FIG. 1) as well as other IV medical fluid delivery applications using catheters, including PIVC catheters, as non-limiting examples.

Figure 5:
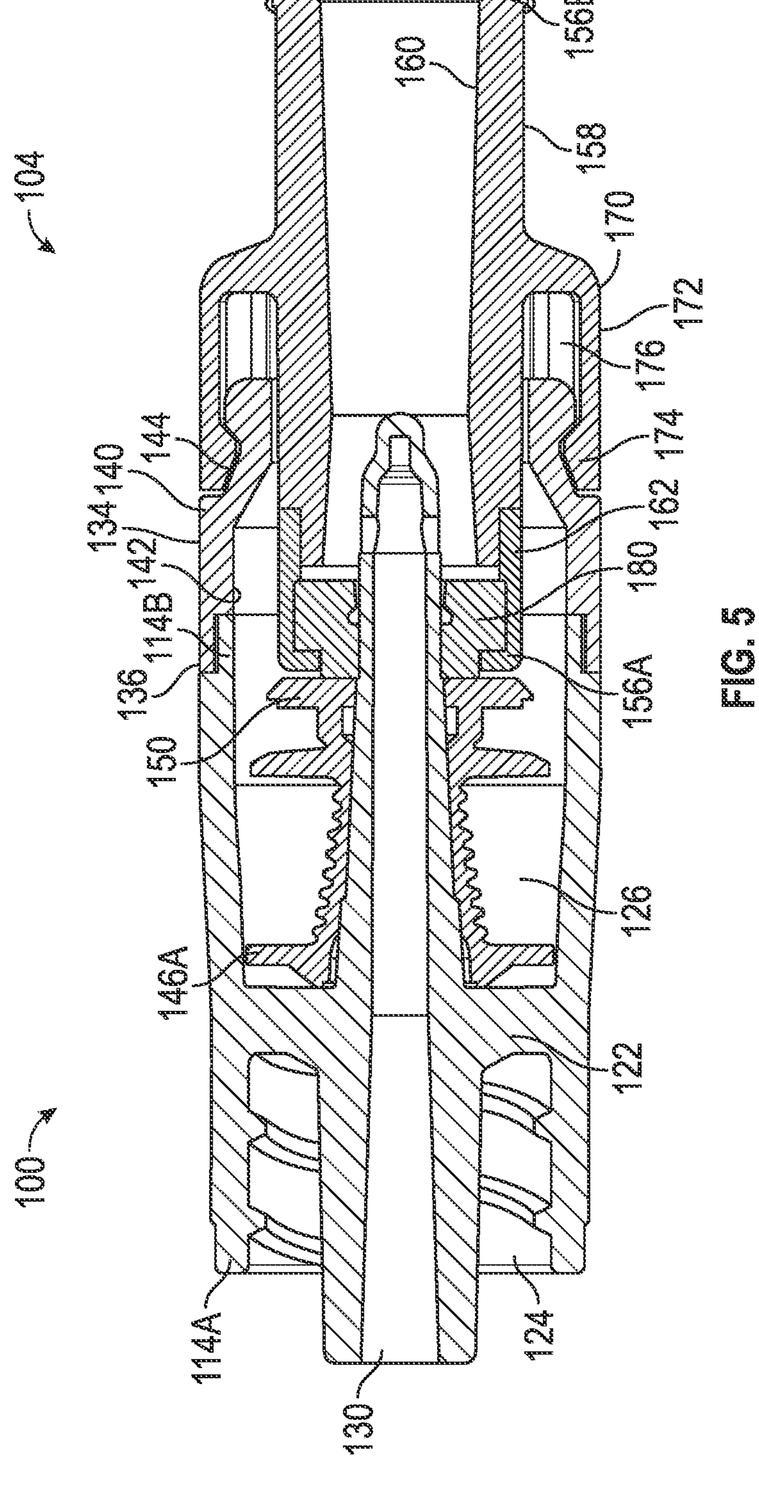
FIG. 5 illustrates a partial cross-sectional view of the fluid connector assembly, in accordance with aspects of the present disclosure.

As shown, the fluid connector assembly 100 includes a connector 102 and a connector 104 configured to be removably coupled with the connector 102. The connector 102 and the connector 104 may be referred to as a first connector and a second connector, respectively. However, “first” and “second” may be interchangeable. Also, each of the connectors 102 and 104 may be referred to as medical connectors. When the connectors 102 and 104 are connected to each other as shown in FIG. 5, a fluid path for medical fluid is established by the fluid connector assembly 100.

In some embodiments, the connector 104 is connected to a medical fluid (not shown). Further, in some embodiments, the connector 102 is connected to a catheter line (not shown) that delivers the medical fluid to a catheter. In this regard, the connector 104 may include a fluid inlet 106 that acts as a fluid receiving location for the fluid connector assembly 100. Also, the connector 102 may include a fluid outlet 110 that acts as a fluid transmission location for the fluid connector assembly 100.

To facilitate the connection to the medical fluid, the connector 104 may include a luer 110. In some embodiments, the luer 110 is female luer designed to mate with a male connector that is connected to the medical fluid. Similarly, to facilitate the connection to the catheter line, the connector 102 may include a luer 112. In some embodiments, the luer 112 is male luer designed to mate with a female connector that is connected to the catheter line. Each of the luers 110, 112 may conform to standards established by the International Organization for Standards ("ISO") to improve patient safety, minimize medical fluid leakage, and reduce misconnection with other connection devices.

Additionally, the connector 102 may include a post 128 passing centrally, or at least approximately centrally, through the connector 102. The post 128 may include a channel 130 that establishes the fluid outlet 110. While the post 128 is illustrated as cylindrical, the post 128 need not be so limited and may have any suitable.

Figure 3:
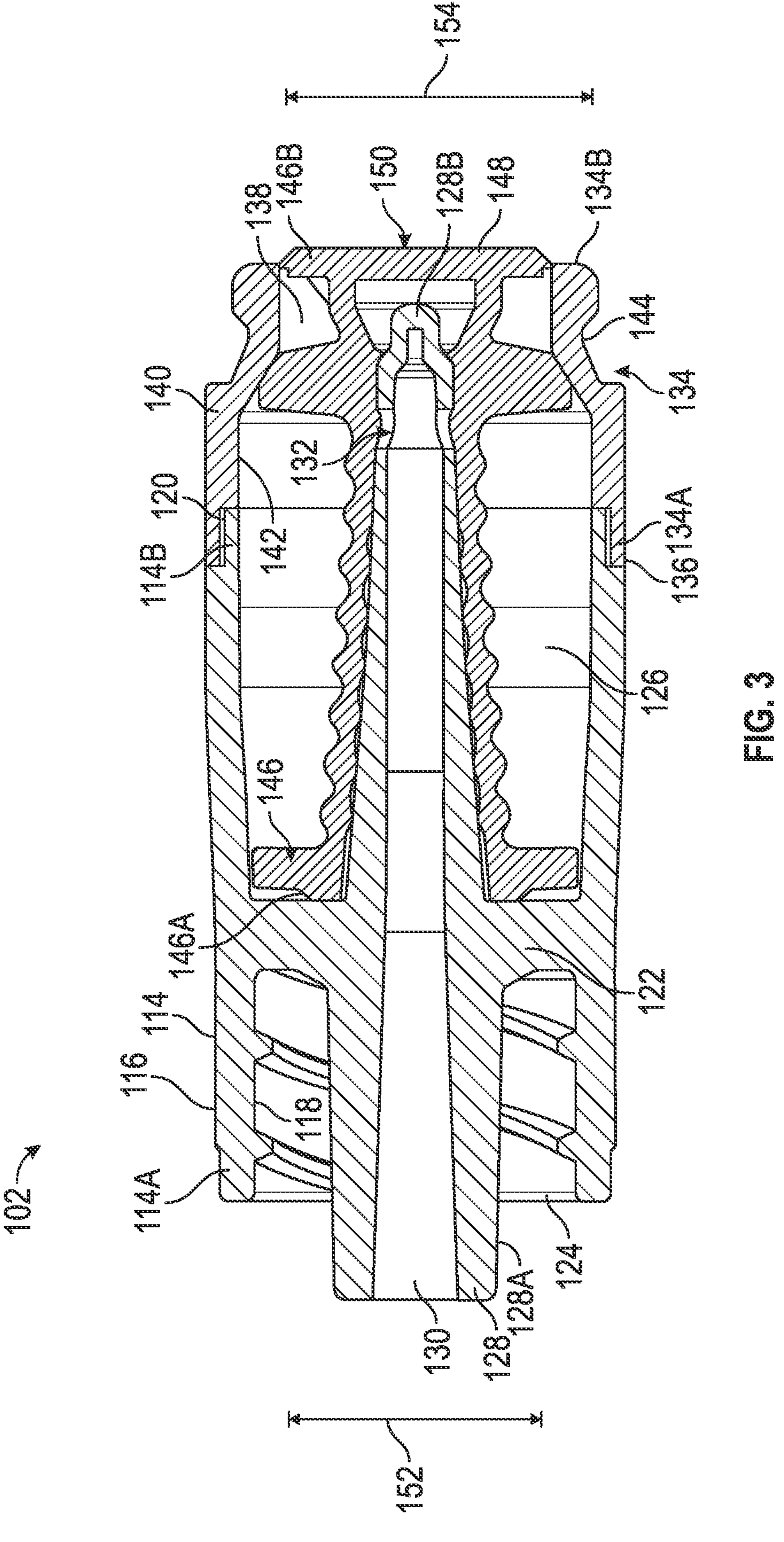
FIG. 3 illustrates a partial cross-sectional view of the connector of the fluid connector assembly, in accordance with aspects of the present disclosure.

Referring to FIG. 3, the connector 102 may include a housing 114 integrated with the luer 112. The housing 114 may include a first end 114A having the integrated luer 112 and a second end 114B opposite the first end 114A configured to couple to a receiving ring 134. The second end 114B of the housing 114 may have a stepped profile with a protruding portion 120 having a reduced thickness relative the thickness of the rest of the housing. The second end 114B of the housing 114 may include an inner diameter 154. Additionally, the first end 114A of the housing 114 includes an inner diameter 152 having a dimension that is less than that of the inner diameter 154. Based on the disparate dimension of the inner diameters 152, 154, in some embodiments, the cavity 126 may include a volume that is greater than that of the cavity 124.

The housing 114 may include an exterior surface 116 and an interior surface 118. The housing 114 may include a hollow, or generally hollow, body that carries one or more components. For example, in addition to the post 128, a compressible member 146, which will be discussed in greater detail, may be housed within the housing 114. The housing 114 may further include a wall 122 extending laterally across the interior of the connector 102 thereby separating the interior of the connector 102 into separate cavities 124, 126. The post 128 may be integrally formed with the wall 122 and extend through each of the cavities 124, 126. The post 128 may include an open first end 128A, a closed second end 128B opposite the first end 128A, and a channel 130 extending through the post 128. The first end 128A may include an opening for the channel 130, which forms the fluid outlet 108. The second end 128B of the post 128 may be a substantially closed end and include one or more apertures, also referred to as flow windows or openings, 132. The openings 132 may be fluidly connected to the channel 130 and the fluid outlet 108.

The connector 102 may further include the receiving ring 134 disposed at, and coupled to, the second end 114B of the housing 114. The receiving ring 134 may include a first end 134A configured to be coupled to the second end 114B and a second end 134B opposite the first end 134A. The first end 134A of the receiving ring 134 may have a stepped profile with a protruding portion 136 that complements the protruding portion 120 of the housing. The second end 134B of the receiving ring 134 may include an opening 138. The receiving ring 134 may have an exterior surface 140 and an interior surface 142. The receiving ring 134 may include one or more notches 144 formed along the exterior surface 140.

As described above, the connector 102 may include a compressible member 146, also referred to a as a silicone valve, disposed within the housing 114. The compressible member 146 may be disposed within the cavity 126 of the housing 114 and extend through the receiving ring 134. The compressible member 146 have a first end 146A positioned proximate a surface of the wall 122 and a second end 146B positioned within the opening 138 of the receiving ring 134 and configured to engage a component of the connector 104. The second end 146B may include an engagement surface 148. The engagement surface 148 may provide a planar, or generally planar, surface that can be readily accessed for cleaning and disinfecting. The engagement surface 148 may further include an opening 150. In some embodiments, the opening 150 may be formed as one or more slits or apertures. The post 128 may extend through the compressible member 146. In other words, the compressible member 146 may extend around an exterior surface of the post 128. The second end 128B of the post 128 may be positioned within an area formed proximate the second end 146B of the compressible member 146.

In some embodiments, the compressible member 146 includes a bellow that can elastically compress. Accordingly, the compressible member 146 can compress by an external force and subsequently return to its original, uncompressed form when the external force is removed. The compressible member 146 may be designed to regulate fluid flow through the connector 102. This will be shown in detail below.

Figure 4:
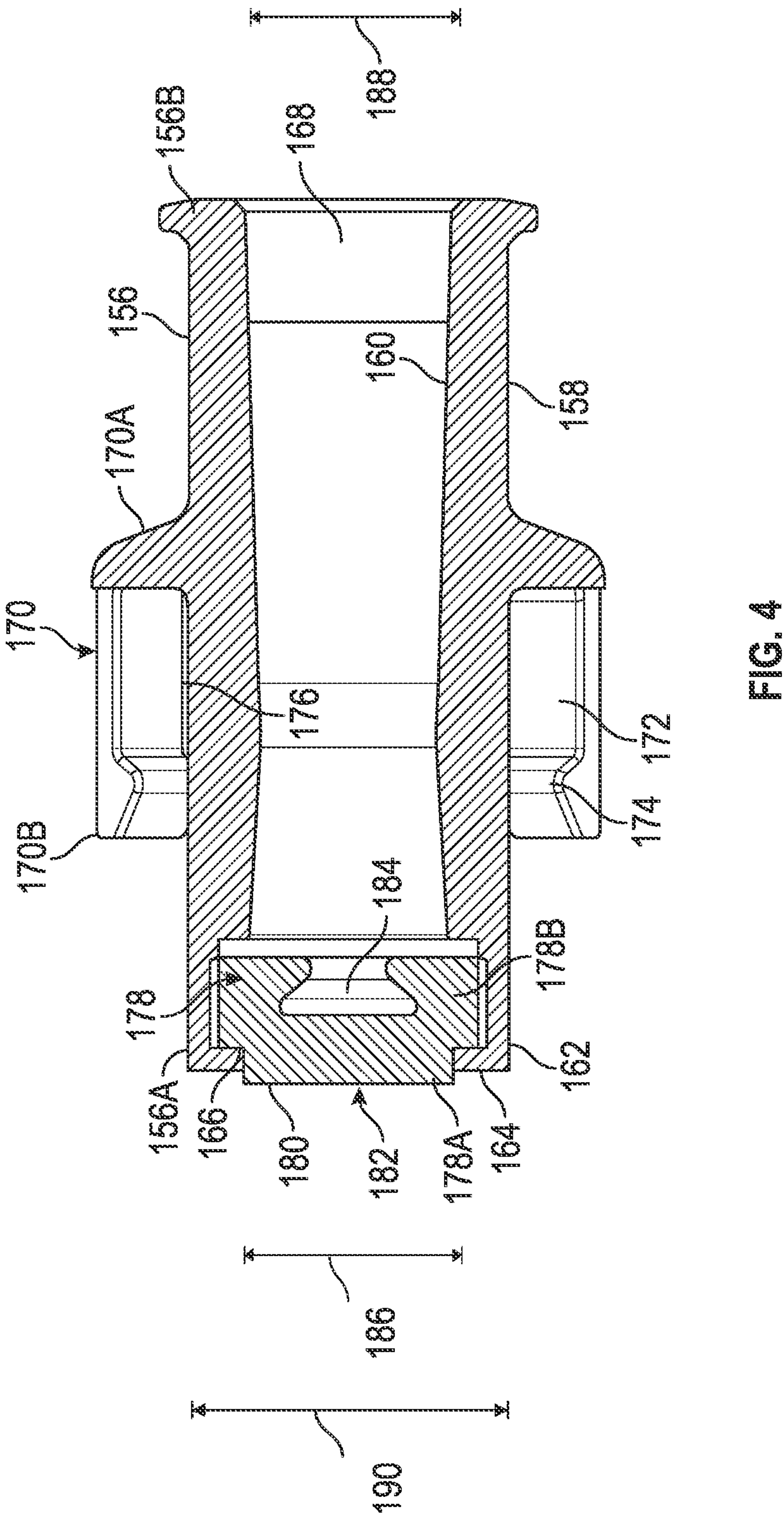
FIG. 4 illustrates a partial cross-sectional view of the fluid connector assembly, in accordance with aspects of the present disclosure.

FIG. 4 illustrates a perspective view of the connector 104, showing additional features, in accordance with aspects of the present disclosure. The connector 104 may include a housing 156. The housing 114 (shown in FIG. 3) and the housing 156 may be referred to as a first housing and a second housing, respectively. However, "first" and "second" may be interchangeable. As shown, the housing 156 may be integrated with the luer 110.

The housing 156 may include a first end 156A configured to mate with the connector 102 when coupled and a second end 156B opposite the first end 156A. The housing 156 may include an exterior surface 158 and an interior surface 160. The housing 156 may include a channel 168 extending through the interior of the housing 156. The housing 156 may include a hollow, or generally hollow, body that carries one or more components. For example, the housing 156 may include a compressible member 178, located, or at least substantially located, in the housing 156.

The second end 156B of the housing 156, where the fluid inlet 106 is located, may include an inner diameter 188. The first end 156A of the housing 156, where the forward portion 162 is located, may include an inner diameter 186 that is greater than the inner diameter 188 of the second end 156B. Additionally, the first end 156A of the housing 156 may include an outer diameter 190. The outer diameter 190 may include a dimension that allows at least a portion of the compressible member 178 and at least a portion of the housing 156 to enter the connector 102 (shown in FIG. 5). In this manner, the dimension of the inner diameter 154 of the second end 114B (shown in FIG. 4) may be greater than the outer diameter 190 of the first end 156A of the housing 156. Also, the dimension of the inner diameter 154 of the second end 114B may be greater than the diameter of the compressible member 178.

The connector 104 may include a forward portion 162 formed within the housing 156 at the first end 156A for receiving a compressible member 178. The housing 156 at the first end 156A may include an inwardly extending rim 164 thereby forming an end of the forward portion 162. The inwardly extending rim 164 may surround an opening 166 at the first end 156A of the housing 156. The exterior surface of the inwardly extending rim 164 may be designed to engage the engagement surface 148

As illustrated, the connector 104 may further include a plurality of snap arms 170 positioned on the exterior surface 158 of the housing 156. In some embodiments, the snap arms 170 may be integrally formed with the housing 156. In other embodiments, the snap arms 170 may be individually formed separate from the housing 156 and coupled to the housing 156 by any suitable means. The snap arms 170 may include a first end 170A coupled to, or integrally formed with, the housing 156, and a second end 170B opposite the first end 170A. The second end 170B may be positioned proximate but spaced away from the exterior surface 158 of the housing 156 such that a gap 176 is formed between an interior surface 172 of the snap arm 170 and the exterior surface 158 of the housing 156. The gap 176 may be sized such that the housing 114 and receiving ring 134 of the connector 102 may be received within the gap 176 when the connectors 102, 104 are coupled. The interior surface 172 of the snap arm 170 may further include protrusion portion 174. The protrusion portion 174 may be sized and shaped to correspond to, and mate with, the notch 144 of the receiving ring 134. The snap arms 170 may be flexible such the second end 170B may flex outwardly with respect to the exterior surface 158, thereby increasing the size of the gap 176, when assembling the fluid connector assembly 100.

In some embodiments, the snap arms 170 may provide a retaining force to maintain the connection/coupling between the connectors 102 and 104 as shown in FIG. 5. The retaining force provided by the snap arms 170 may also be equated to a threshold force that maintains the connection/coupling between the connectors 102 and 104. However, when an external force, such as a pulling force provided to one or more of the connectors 102 and 104, is applied to at least one of the connectors 102 and 104 and is greater than the threshold force, the snap arms 170 may no longer maintain the connection/coupling between connectors 102 and 104, and the connectors 102 and 104 may decouple from each other. When this occurs, the forward portion 162 and the housing 156 of the connector 104 may be removed from the housing 114 of the connector 102.

The connector 104 may further include the compressible member, also referred to as an elastomeric plug. 178 disposed within the housing 156. In particular, the compressible member 178 may be disposed within the forward portion 162. The compressible member 178 may include a first end 178A positioned within the opening 166 and a second end 178B opposite the first end 178A. The first end 178A may include an engaging surface 180. The first end 178A may project out of the forward portion 162 of the housing 156 such that the engaging surface 180 is positioned forward of the inwardly extending rim 164. In other words, when the connectors 102, 104 are disconnected, the engaging surface 180 may be form an exterior surface of the housing 156. This positioning may allow the engaging surface 180 to be readily accessed for cleaning and disinfecting. The engaging surface 180 may include one or more apertures 182.

The compressible member 178 may further include an opening 184 formed at the second end 178B. While FIG. 4 shows a singular opening formed in the compressible member 178, the number of openings may vary. For example, in some embodiments, one or more openings may be formed in the compressible member 178. In either event, each opening(s) may include any feature shown and described for the openings 184. Fluid flowing through the fluid inlet 106 may pass through the compressible member 178 via the aperture 182. In some embodiments, the compressible member 178 includes a bellow that can elastically compress. Accordingly, the compressible member 178 can compress by an external force and subsequently return to its original, uncompressed form when the external force is removed. The compressible member 178 is designed to regulate fluid flow through the connector 104. This will be shown in detail below.

Based on the connection, a seal is formed between the housing 156 and the compressible member 178 such that fluid does not flow between the housing 156 and the compressible member 178 when the connector 104 is disconnected from the connector 102.

Based on the position of the compressible member 178 shown in FIG. 4, the connector 104 may prevent fluid flow therethrough. In other words, fluid that enters the channel 168 via the fluid inlet 106, may be prevented from passing through the forward portion 162 due to the positioning and expanded state of the compressible member 178.

In order to promote fluid through the connectors 102,104, when the fluid connector assembly 100 is assembled, the respective compressible members 146, 178 may be actuated, or displaced, to uncover respective openings in the connectors 102,104.

FIG. 5 illustrates a partial cross-sectional view of the fluid connector assembly 100, showing the connectors 102 and 104 engaged, and further showing actuation of the compressible members 146 and 178, in accordance with aspects of the present disclosure. The fluid connector assembly 100 can be assembled by coupling the connectors 102, 104. To couple the connectors, 102, 104, the respective engagement surfaces 148, 180 can be positioned such that they contact one another. Due to the respective dimensions of the inner diameter 154 of the connector 102 and the outer diameter 186 of the connector 104, the connector 104 may be received within the opening 138 of the receiving ring. Force, or pressure, may then be applied to either, or both of, the connectors 102, 104. As pressure is applied, the compressible members 146, 178 may begin to deform. For example, the compressible member 146 may deform such that the second end 146B of the compressible member 146 moves in a direction towards the first end 146A thereby positioning the second end 146B within the cavity of the receiving ring 134. As the compressible member 146 deforms under pressure, the second end 128B of the post 128 may protrude through the opening 150 of the engagement surface 148. The second end 146B of the compressible member 146 may continue to deform until the opening 132 of the post 128 are exposed thereby allowing fluids to enter the channel 130 of the post 128. Similarly, as pressure is applied to one or both of the connectors 102, 104, the first end 156A of the connector 104 may be moved within the receiving ring 134 and the compressible member 178 may deform such that the first end 178A of the compressible member 178 moves within the forward portion 162 toward the second end 178B. As the connector 104 is moved within the housing 114 of the connector 102, the second end 128B of the post 128 may contact the engagement surface 180 of the compressible member 178. In some embodiments, the post 128 may extend through the aperture 182 of the engagement surface 180.

The forward portion 162 of the connector 104 may be inserted into the receiving ring 134 and the housing 114 and can be at least partially inserted into the cavity 126 of the housing 114. The connectors 102, 104 may remain coupled together via the interconnection of the snap arms 170 and the notch 144. In particular, the connectors 102, 104 can be held together via a friction or interference fit between the protrusion portion 174 of the snap arms 170 and the notches 144.

Upon insertion of the housing 156, the forward portion 162 may engage the compressible member 146 of the connector 102. For example, as shown in FIG. 5, the compressible member 146 of the connector 102 may engage the compressible member 178 of the connector 104 such that the engaging surface 148 of the compressible member 146 contacts the engaging surface 180 of the compressible member 178. From the perspective of the compressible member 146, an external force may be provided by at least the forward portion 162 and/or engaging surface 180. Thus, based on the insertion and engagement described above, the engaging surface 180 and/or forward portion 162 may provide a force that actuates the compressible member 146.

For example, the actuation of the compressible member 146 may include a compression of the compressible member 146. In this manner, the compression of the compressible member 146 may cause the compressible member 146 to reduce in size, to move relative to the post 128 thereby exposing the opening 132 of the post 128. Accordingly, the opening 132 of the post 128 may be uncovered by the compressible member 146 and such that the compressible member 146 no longer provides a seal against fluid entry into the opening 132. As such, the compressible member 146, located in the housing 114, may be designed to actuate, e.g., compress, in response to a force received by an external object, or objects, of the connector 104.

In some embodiments, the post 128 of the connector 102 may engage the compressible member 146 of the connector 102 at or near the same time of insertion of the insertion of the forward portion 162 and the housing 156 into the housing 114. For example, the second end 128B of the post 128 may engage the engaging surface 180 of the compressible member 178 through the opening 150. From the perspective of the compressible member 178, an external force may be provided by at least the post 128. As the forward portion 162 and the housing 156 are further inserted into the housing 114, the post 128 may provide a force that actuates the compressible member 178. For example, the actuation of the compressible member 178 may include a compression of the compressible member 178, thereby reducing the size of the compressible member 178, forcing the first end 178A of the compressible member 178 out of the opening 166 of the forward portion thereby breaking the seal between the compressible member 178 and the first end 156A of connector 104. Also, the actuation of the compressible member 178 may allow the post 128 to pass through the opening 166 of the housing 156 and extend into an interior of the housing 156 at the forward portion 162. Moreover, the post 128 may pass through the opening 166 such that the opening 132 of the post 128 may also pass through the opening 166 and is positioned within an interior of the housing 156. Accordingly, the compressible member 178, located in the housing 156, may be designed to actuate, i.e., compress, in response to a force received by an external object, or objects, of the connector 102.

Based upon the configuration of the fluid connector assembly 100 a fluid path may be established. Accordingly, a fluid, including a medical fluid, can pass through the fluid connector assembly 100 downstream from the connector 104 to the connector 102. As shown, fluid can enter the fluid inlet 106 of the housing 156 and subsequently pass through the compressible member 178 by way of the opening 184 of the compressible member 178. The fluid can then pass through the opening 132 of the post 128, and then through the channel 130 of the post 128. The fluid can exit the fluid connector assembly 100 through the fluid outlet 108 of the housing 114.

As described above, the decoupling of the connectors 102 and 104 may result from an external force applied to one or more of the connectors 102 and 104, where the external force exceeds the threshold force provided by the snap arms 170 that maintain a connection between the connectors 102 and 104.

When the connectors 102, 104 are decoupled, the force applied to the compressible members 146, 178 of the connectors 102, 104, respectively, may be removed such that the compressible members 146, 178 may decompress and expand such that the compressible members 146, 178 return to their original shapes. For example, during expansion of the compressible member 146, the second end 146B of the compressible member 146 may move toward the second end 134B of the receiving ring 134 until the compressible member 146 has returned to its original shape such of the and the second end 146B is positioned within the opening 138 of the receiving ring 134. Similarly, during expansion of the compressible member 178, the first end 178A may move toward the opening 166 until the compressible member 178 has returned to its original shape such that the first end 178A is positioned within the opening 166. As a result, fluid may be unable to flow upstream through the connector 102 and pass through the opening 132 of the post 128.

Each of the compressible members 146 and 178 may be used as a valve to regulate fluid through the fluid connector assembly 100. Based on their elastic, springlike properties, each of the compressible members 146 and 178 may automatically return to their respective shapes when external forces are no longer acting on them. Beneficially, the compressible members 146 and 178 may spring back in response to a decoupling between the connectors 102 and 104 to provide a relatively quick sealing effect. Accordingly, blood losses, IV fluid losses, and medical delivery delays can be limited or prevented, based on one or more properties of the compressible members 146 and 178, when integrating the fluid connector assembly 100 into an IV set and catheter.

In some embodiments, the fluid connector assembly 100 may further include a connecting mechanism 200, 300, 400 that activates in when the fluid connector assembly 100 is decoupled.

Figure 6A:
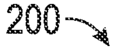
FIGS. 6A-6B illustrate views of the connecting mechanism of the fluid connector assembly, in accordance with aspects of the present disclosure.
Figure 6A:
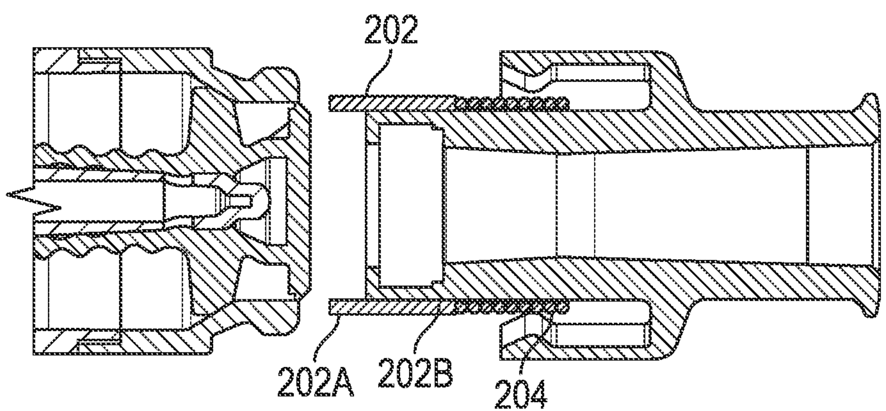
Figure 6B:
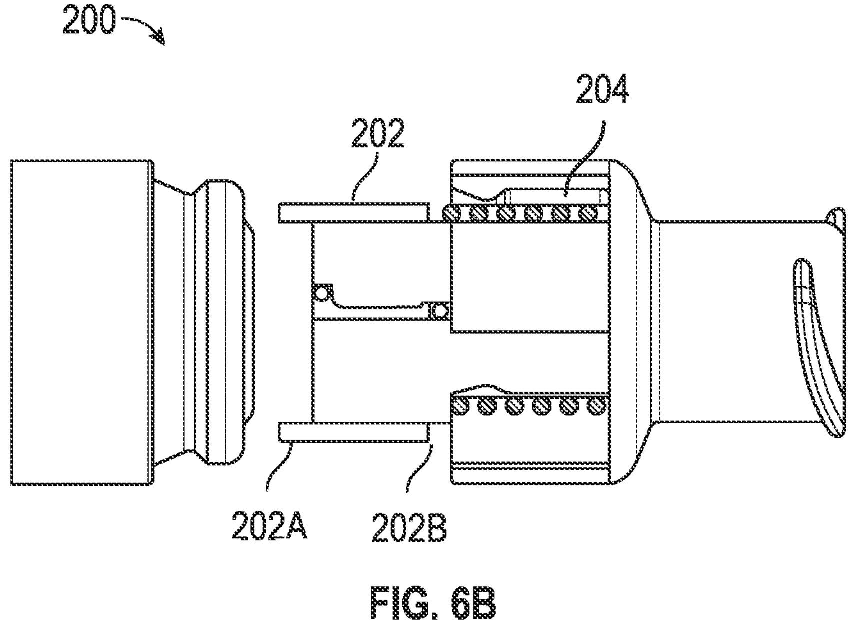

Referring to FIGS. 6A-6B, the connecting mechanism 200 may include one or more projections 202 coupled to the housing 156 of the connector 104. The projections 202 may be coupled to the housing 156 of the connector 104 proximate the snap arms 170. The connecting mechanism 200 may further include a biasing member 204, for example a spring mechanism. In some embodiments, the projections 202 may be coupled to the housing 145 via the biasing member 204. The projections 202 may extend longitudinally along the housing 156 and extend past the engaging surface 180. The projections 202 may have a stowed position and a deployed position. In the stowed position, the projections 202 may be retracted towards the connector 104 against a bias of the biasing member 204. In the deployed position, the projections 202 may be extended via the biasing member 204. The biasing member 204 may bias the projections 202 in the deployed position.

The connector 104 may further include one or more slots 206 for receiving the projections 202. In some embodiments, the slots 206 may be disposed on the housing 156 of connector 104 adjacent to the projections 202. The slots 206 may be sized and shaped to receive the projections 202 such that the projections 202 may be held within the slots 206 via friction fit or keyed interference.

When the fluid connector assembly 100 is disconnected (i.e., when the connectors 102, 104 are separated), the projections 202 may be extended via a force of the biasing member 204 such that the projections 202 may be extended to the deployed position such that ends of the projections 202 extend past the engaging surface 180 of the connector 104. With the projections 202 in the deployed position, the projections 202 may be locked within the slots 206 such that the connector 102 and the connector 104 may be prevented from being easily recoupled without adjustment of the connecting mechanism 200.

To reconnect the fluid connector assembly 100, a user may rotate the connector 104 to unlatch the projections. Once the connector 104 has been rotated, the projections 202 may be displaced such that the projections 202 are free of the slot 206 and, thus, allowing the connectors 102, 104 to be reconnected.

Figure 7:
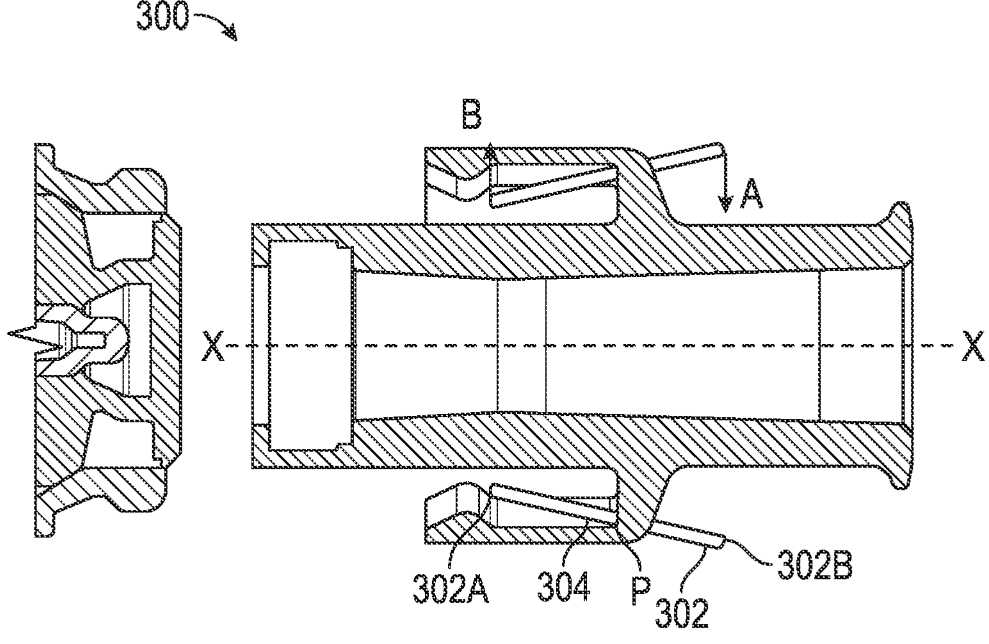
FIG. 7 illustrates a partial cross-sectional view of a connecting mechanism of the fluid connector assembly, in accordance with aspects of the present disclosure.

Referring to FIG. 7, in some embodiments, the connector 104 may include connecting mechanism 300 having one or more projections 302. The projections 302 may be coupled to the snap arms 170. The projections 302 may include a first end 302A disposed within the gap 176 formed between the snap arm 170 and the housing 156, and a second end 302B opposite the first end 302A. The second end 302B may extend in a direction toward the first end 156A of the connector 104 such that the second end 302B extends out from and beyond the snap arm 170. The projections 302 may be coupled to the snap arms 170 at a position between the first end 302A and the second end 302B. The projections 302 may be biased via a biasing member 304. The biasing member 304 may be any suitable mechanism, including, but not limited to, torsion springs, spiral springs, compression springs, tension springs.

The projections 302 may have a stowed position, also referred to as the first position, and a deployed position, also referred to as the second position. In the stowed position, the first end 302A of the projection 302 may be positioned within the gap 176 such that the first end 302A is proximate an interior surface of the snap arm 170 and the second end 302B may be angled away from the housing 156 of the connector 104. In other words, the projections 302 may be positioned at an angle with respect to a central longitudinal axis X of the connector 104 such that first end 302A is disposed closer to the central longitudinal axis X, and consequently the housing 156, than the second end 302B. In the deployed position, the first end 302A may directly contact the interior surface of the snap arm 170 and the second end 302B may be rotated such that the second end 302B is positioned closer to the central longitudinal axis X, and consequently the housing 156. The projections 302 may be biased to a stowed position via the biasing member 304.

In the event the fluid connector assembly 100 is disconnected, the projections 302 may be actuated to reconnect the connector 102 and the connector 104. To reconnect the connectors 102, 104, the projections 302 may be engaged to move the projections 302 from the stowed position to the deployed position. For example, a force may be applied to the second end 302B to pivot the second end 302B towards the housing 156 thereby causing the first end 302A to pivot towards the interior surface of the snap arms 170. When a sufficient amount of force is applied to the second end 302B of the projections 302, the snap arms 170 may be displaced in a lateral direction with respect to the housing 156 thereby allowing the connector 104 to be coupled to the connector 102. Once the connector 104 and the connector 102 are coupled such that the snap arms 170 are positioned with in the notch 144 of the receiving ring 134, the force may be released such that the biasing member 304 biases the projections 302 towards the stowed position.

Figure 8:
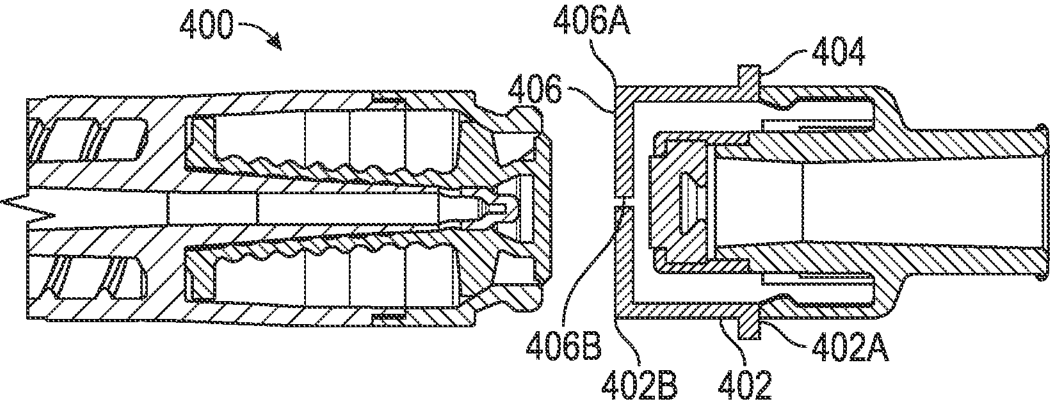
FIG. 8 illustrates a partial cross-sectional view of a connecting mechanism of the fluid connector assembly, in accordance with aspects of the present disclosure.

In some embodiments, as illustrated in FIG. 8, the connector 104 may include the connecting mechanism 400 formed as extended tabs extending from each of the snap arms 170. The connecting mechanism 400 may include a projection 402 having a first end 402A positioned proximate the snap arms 170 and a second end 402B opposite the first end 402A. The connecting mechanism 400 may further include a push arm, or handle, 404 disposed on the first end 402A of the projection 402. The push arm 404 may project radially from the first end 402A of the projection 402. The connecting mechanism 400 may further include a cover portion 406 disposed on the second end 402B of the projection 402. The cover portion 406 may project at an angle with respect to the projection 402 such that the cover portion 406 from a first projection 402 and the cover portion 406 from a second projection 402 form a cover shielding the engaging surface 180 of the compressible member 178 from the surrounding environment. In some embodiments, as illustrated in FIG. 7, the connecting mechanism 400 includes a first projection 402 and a second projection 402 formed on opposing sides of the connector 104. Each of the first and second projections 402 may include the push arm 404, projection 402, and cover portion 406 described above.

The projection 402 may have a stowed position and deployed position. In the stowed position, also referred to as the resting position or the first position, the projection 402 is disposed approximately parallel to the longitudinal axis X of the connector 104 and the cover portion 406 is positioned along a plane approximately parallel to the engaging surface 180 of the compressible member 178 such that cover portion 406 shields the engaging surface 180. In some embodiments, surfaces of the cover portion 406 of each of the first and second projections 402, may directly contact each other in the stowed position. In other embodiments, there may be a gap formed between the cover portions 406 of each of the first and second projections 402. In the deployed position, the cover portions 406 be spaced apart such that the engaging surface 180 is exposed thereby allowing for reconnection of the connectors 102, 104. The connecting mechanism 400 may be biased towards the stowed position via a biasing member 408. The biasing member 408 may be any suitable mechanism, including, but not limited to, torsion springs, spiral springs, compression springs, tension springs.

Next operation of the connecting mechanism 400 is explained in the event the fluid connector assembly 100 is disconnected. To operate the connecting mechanism 400, a user may apply a force to the push arm 404 which may thereby move the cover portions 406 from the stowed position to the deployed position, against a force of the biasing member 408. Once the cover portions 406 have been spaced apart to a suitable distance to allow engaging surface 180 of the compressible member 178 to mate and contact the engaging surface 148 of the compressible member 146, the connector 102 and the connector 104 may be coupled. After the connectors 102, 104 are coupled, the push arms 404 may be released allowing the cover portions 406 to return towards the stowed position via the biasing member 408. In this position, the projections 402 may extend along the receiving ring 134 and the housing 114 of the connector 102 and the cover portions 406 may contact an exterior surface of the housing 114 of the connector 102.

The features of the present disclosure provide first and second compressible members that can be used as valves to regulate a fluid pathway therebetween. The first and second compressible members are located in a first and a second connector, respectively. If the first and second connectors are separated, whether unintentionally or intentionally, the fluid pathway for each of the first and second compressible members become closed or obstructed to prevent fluid loss therefrom. The features of the present disclosure also provide that upon separation of the first and second compressible members, any of the first and second compressible members can be cleaned and disinfected, and the first and second compressible members can be once again coupled together to form a fluid pathway therebetween.

ILLUSTRATION OF SUBJECT TECHNOLOGY AS CLAUSES

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1, clause 11, clause 17, clause, clause 23, clause 26, or clause 29. The other clauses can be presented in a similar manner.

Clause 1. A fluid connector assembly, comprising: a first connector, comprising: a first housing comprising a cavity, a post disposed in the first housing, the post comprising an opening, and a first compressible member surrounding at least a portion of the post; a second connector configured to couple with the first connector, the second connector comprising: a second housing, a second compressible member disposed within the second housing; and a connecting mechanism coupled to the second connector for coupling the first connector and the second connector, the connecting mechanism comprising: at least one projection extending from the second housing for actuating the connecting mechanism, wherein actuation of the at least one projection allows the first connector and the second connector to be coupled.

Clause 2. The fluid connector assembly described above, wherein: the second connector is held in the cavity by a threshold force, and responsive to an external force, greater than the threshold force, applied to at least one of the first connector and the second connector that removes the second housing from the cavity: the first compressible member seals the first opening, and the second compressible member seals the second opening.

Clause 3. The fluid connector assembly described above, wherein the connecting mechanism further comprises a biasing member for biasing the at least one projection.

Clause 4. The fluid connector assembly described above, wherein the connecting mechanism comprise a stowed position and a deployed position, and wherein the connecting mechanism is biased to the stowed position via the biasing member.

Clause 5. The fluid connector assembly described above, wherein the connecting mechanism further comprises at least one slot disposed on the second connector and proximate the at least one projection, and wherein, when the first connector and the second connector are decoupled, the at least one projection is urged to the deployed position via the biasing member such that the at least one projection moves into at least one slot.

Clause 6. The fluid connector assembly described above, wherein, reconnection of the first connector and the second connector requires movement of the at least one projection out of the at least one slot.

Clause 7. The fluid connector assembly described above, wherein the connecting mechanism comprise a stowed position and a deployed position, and wherein the connecting mechanism is biased to the stowed position via the biasing member.

Clause 8. The fluid connector assembly described above, wherein the at least one projection comprises: a first end positioned within a gap formed between the at least one snap arm and the second housing; and a second end opposite the first end, wherein the at least one projection is positioned at an angle relative a longitudinal axis of the second connector, and wherein the first end is positioned closer to the second housing than the second end.

Clause 9. The fluid connector assembly described above, wherein, when a force is applied to the second end of the at least one projection, the connecting mechanism is actuated such that the at least one projection moves from the stowed position to the deployed position.

Clause 10. The fluid connector assembly described above, wherein, in the deployed position, the first end of the at least one projection is moved away from the second housing, and the second end of the at least one projection is moved toward the second housing.

Clause 11. The fluid connector assembly described above, wherein the connecting mechanism further comprises: a handle for actuating the at least one projection; and a cover portion for covering an engaging portion of the second connector, wherein the handle is disposed on a first end of the projection and the cover portion is disposed on a second end of the projection opposite the handle.

Clause 12. The fluid connector assembly described above, wherein, when a force is applied to the handle, the connecting mechanism is actuated such that the at least one projection moves from a stowed position to a deployed position.

Clause 13. The fluid connector assembly described above, wherein, in the deployed position, the cover portion is actuated such that an end of the second compressible member is exposed thereby allowing the first connector and the second connector to be coupled.

Clause 14. A method for coupling a fluid connector assembly, the method comprising: providing a first connector, the first connector comprising: a first housing comprising a cavity; a post disposed in the first housing, the post comprising an opening; and a first compressible member surrounding at least a portion of the post; providing a second connector configured to couple to the first connector, the second connector comprising: a second housing; a second compressible member disposed within the second housing; and providing a connecting mechanism configured to couple the first connector to the second connector actuating the connecting mechanism; coupling first connector and the second connector; releasing the connecting mechanism thereby allowing the connecting mechanism to retain the first connector and the second connector in a coupled state.

Clause 15. The method described above, wherein the connecting mechanism comprises at least one projection and at least one slot for receiving the at least one projection; and wherein actuating the connecting mechanism comprises: rotating the second connector such that the at least one projection is displaced from the at least one slot.

Clause 16. The method described above, wherein the second connector comprises at least one snap arm disposed on the second housing and the connecting mechanism comprises at least one projection extending from the second housing proximate the at least one snap arm.

Clause 17. The method described above, wherein actuating the connecting mechanism comprises: applying a force to a first end of the at least one projection thereby causing the at least one projection to pivot and displace the at least one snap arm a distance away from the second housing.

Clause 18. The method described above, wherein the connecting mechanism further comprises a handle on a first end of the projection and a cover portion disposed on a second end opposite the first end.

Clause 19. The method described above, wherein actuating the connecting mechanism comprises: applying a force to the handle thereby causing the cover portion to move relative an end of the second housing.

Clause 20. A fluid connector assembly, comprising: a first connector, comprising: a first housing comprising a cavity, a post disposed in the first housing, the post comprising an opening, and a first compressible member surrounding at least a portion of the post; a second connector configured to couple with the first connector, the second connector comprising: a second housing, a second compressible member disposed within the second housing configured to contact the first compressible member when the first connector and second connector are coupled, at least one snap arm disposed on an exterior surface of the second housing for retaining the fluid connector assembly in a coupled state; and a connecting mechanism coupled to the second connector for coupling the first connector and the second connector, the connecting mechanism comprising: at least one projection extending from the at least one snap arm for actuating the connecting mechanism, the at least one projection having a stowed position and an deployed position, wherein the at least one projection is moved toward the deployed position in response to an external force thereby actuating the connecting mechanism, wherein, when the first connector and the second connector are decoupled, actuation of the at least one projection is required to recouple the first connector and the second connector.

FURTHER CONSIDERATIONS

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A fluid connector assembly, comprising:

a first connector, comprising:

a first housing comprising a cavity, a post disposed in the first housing, the post comprising an opening, and a first compressible member surrounding at least a portion of the post;

a second connector configured to couple with the first connector, the second connector comprising:

a second housing, a second compressible member disposed within the second housing;

at least one snap arm disposed on an exterior surface of the second housing for engaging against the first connector; and a connecting mechanism coupled to the second connector for coupling the first connector and the second connector, the connecting mechanism comprising at least one projection extending from the second housing for actuating the connecting mechanism, the at least one projection comprising a first end positioned within a gap formed between the at least one snap arm and the second housing, and second end opposite the first end;

wherein actuation of the at least one projection from a stowed position to a deployed position such that the first connector is couplable to the second connector.

2. The fluid connector assembly of claim 1, wherein:

the second connector is held in the cavity by a threshold force, and responsive to an external force, greater than the threshold force, applied to at least one of the first connector and the second connector that removes the second housing from the cavity;

the first compressible member seals the first opening, and the second compressible member seals the second opening.

3. The fluid connector assembly of claim 1, wherein the connecting mechanism further comprises a biasing member for biasing the at least one projection.

4. The fluid connector assembly of claim 3, wherein the biasing member is positioned such that the at least one projection is biased toward the stowed position.

5. The fluid connector assembly of claim 4, wherein the biasing member comprises any of a torsion spring, a spiral spring, a compression spring, or a tension spring.

6. The fluid connector assembly of claim 3, wherein the connecting mechanism is biased to the stowed position via the biasing member.

7. The fluid connector assembly of claim 1, wherein, in the stowed position, the at least one projection comprises the at least one projection is positioned at an angle relative a longitudinal axis of the second connector, such that the first end is positioned closer to the second housing than the second end.

8. The fluid connector assembly of claim 1, wherein, when a force is applied to the second end of the at least one projection, the connecting mechanism is actuated such that the at least one projection moves from the stowed position toward the deployed position.

9. The fluid connector assembly of claim 1, wherein, the at least one projection is configured such that the first end of the at least one projection moves in a direction away from the second housing, and the second end of the at least one projection moves in a direction toward the second housing when the at least one projection is moved from the stowed position toward the deployed position.

10. The fluid connector assembly of claim 1, wherein the first housing comprises a receiving ring configured to be positioned in the gap between the at least one snap arm and the second housing when the second connector is coupled with the first connector.

11. The fluid connector assembly of claim 10, wherein the receiving ring comprises a notch and the at least one snap arm comprises a protrusion such that the protrusion is configured to engage against the notch when the second connector is coupled with the first connector.

12. A method for coupling a fluid connector assembly, the method comprising:

providing a first connector, the first connector comprising:

a first housing comprising a cavity;

a post disposed in the first housing, the post comprising an opening; and a first compressible member surrounding at least a portion of the post;

providing a second connector configured to couple to the first connector, the second connector comprising:

a second housing;

a second compressible member disposed within the second housing;

at least one snap arm disposed on an exterior surface of the second housing for engaging against the first connector; and providing a connecting mechanism configured to couple the first connector to the second connector, the connecting mechanism comprising at least one projection extending from the second housing and having a first end positioned within a gap between the at least one snap arm and the second housing, and second end opposite the first end;

actuating the connecting mechanism from a stowed position to a deployed position;

coupling the first connector and the second connector; and releasing the connecting mechanism thereby allowing the connecting mechanism to retain the first connector and the second connector in a coupled state.

13. The method of claim 12, wherein actuating the connecting mechanism comprises applying a force to the second end of the at least one projection thereby causing the at least one projection to pivot and displace the at least one snap arm a distance away from the second housing.

14. The method of claim 12, wherein the connecting mechanism further comprises a handle on a first end of the projection and a cover portion disposed on a second end opposite the first end.

15. The method of claim 14, wherein actuating the connecting mechanism comprises applying a force to the handle thereby causing the cover portion to move relative to an end of the second housing.

16. A fluid connector assembly, comprising:

a first connector, comprising:

a first housing comprising a cavity, a post disposed in the first housing, the post comprising an opening, and a first compressible member surrounding at least a portion of the post; and a second connector configured to couple with the first connector, the second connector comprising:

a second housing, a second compressible member disposed within the second housing configured to contact the first compressible member when the first connector and second connector are coupled, at least one snap arm disposed on an exterior surface of the second housing for retaining the fluid connector assembly in a coupled state; and a connecting mechanism coupled to the second connector for coupling the first connector and the second connector, the connecting mechanism comprising at least one projection extending from the at least one snap arm for actuating the connecting mechanism, the at least one projection having a stowed position and a deployed position, wherein the at least one projection is moved toward the deployed position in response to an external force thereby actuating the connecting mechanism, wherein, when the first connector and the second connector are decoupled, actuation of the at least one projection is required to recouple the first connector and the second connector.

17. The fluid connector assembly of claim 16, wherein the connecting mechanism comprises a biasing member for biasing the at least one projection toward the stowed position.

18. The fluid connector assembly of claim 17, wherein the first housing comprises a receiving ring configured to be positioned in the gap between the at least one snap arm and the second housing when the second connector is coupled with the first connector.

19. The fluid connector assembly of claim 18, wherein the receiving ring comprises a notch and the at least one snap arm comprises a protrusion such that the protrusion is configured to engage against the notch when the second connector is coupled with the first connector.

* * * * *